(12) United States Patent
Verin et al.

(10) Patent No.: US 6,231,494 B1
(45) Date of Patent: May 15, 2001

(54) MEDICAL DEVICE WITH RADIATION SOURCE

(75) Inventors: Vitali Verin; Youri Popowski, both of Geneva (CH)

(73) Assignee: Schneider (Europe) A.G., Bulach (CH)

( * ) Notice: Subject to any disclaimer, the term of this patent is extended or adjusted under 35 U.S.C. 154(b) by 0 days.

(21) Appl. No.: 08/972,107

(22) Filed: Nov. 17, 1997

Related U.S. Application Data

(62) Division of application No. 08/489,464, filed on Jun. 12, 1995, now Pat. No. 5,688,220.

(30) Foreign Application Priority Data

Jun. 10, 1994 (EP) .................................................. 94108913

(51) Int. Cl.$^7$ .................................................. A61N 5/00
(52) U.S. Cl. .................................................. 600/1
(58) Field of Search .................................................. 600/1–8

(56) References Cited

U.S. PATENT DOCUMENTS

| | | |
|---|---|---|
| 1,442,051 | 1/1923 | Cummings . |
| 2,546,761 | 3/1951 | Loftus ................................... 128/1.2 |
| 2,862,108 | 11/1958 | Meilink ................................. 250/106 |
| 2,955,208 | 10/1960 | Stevens ................................. 250/108 |
| 3,060,924 | 10/1962 | Rush ..................................... 128/1.2 |
| 3,147,383 | 9/1964 | Prest ..................................... 250/108 |
| 3,324,847 | 6/1967 | Zoumboulis ......................... 128/1.2 |
| 3,505,991 | 4/1970 | Hellerstein et al. ................. 128/1.1 |
| 3,643,096 | 2/1972 | Jeffries, Jr. et al. ............. 250/108 R |
| 3,669,093 | 6/1972 | Sauerwein et al. ................. 128/1.1 |
| 3,674,006 | 7/1972 | Holmer ................................... 600/7 |
| 3,750,653 | 8/1973 | Simon ................................... 128/1.2 |
| 3,811,426 | 5/1974 | Culver et al. ........................ 128/1.2 |
| 3,861,380 | 1/1975 | Chassagne et al. ................. 128/1.2 |
| 3,866,050 | 2/1975 | Whitfield ............................. 250/497 |
| 3,927,325 | 12/1975 | Hungate et al. ..................... 250/435 |
| 3,970,073 | 7/1976 | Greene ................................... 128/1.2 |
| 4,096,862 | 6/1978 | DeLuca ................................. 128/348 |
| 4,220,864 | 9/1980 | Sauerwein et al. ................. 250/497 |
| 4,225,790 | 9/1980 | Parsons, Jr. et al. ................. 250/497 |
| 4,244,357 | 1/1981 | Morrison ............................. 128/1.2 |
| 4,281,252 | 7/1981 | Parsons, Jr. et al. ................. 250/497 |
| 4,314,157 | 2/1982 | Gaines ................................. 250/497 |
| 4,364,376 | 12/1982 | Bigham ............................... 128/1.1 |
| 4,402,308 | 9/1983 | Scott ..................................... 128/1.2 |
| 4,584,991 | 4/1986 | Tokita et al. ........................ 128/1.1 |
| 4,588,395 | 5/1986 | Lemelson ............................... 604/59 |
| 4,631,415 | 12/1986 | Sauerwein et al. ............... 250/497.1 |
| 4,697,575 | 10/1987 | Horowitz ............................. 128/1.2 |
| 4,702,228 | 10/1987 | Russell, Jr. et al. ................. 128/1.2 |
| 4,706,652 | 11/1987 | Horowitz ............................. 128/1.2 |

(List continued on next page.)

FOREIGN PATENT DOCUMENTS

| | | |
|---|---|---|
| 2166915 | 8/1996 | (CA) . |
| 9102312 | 8/1992 | (DE) . |

(List continued on next page.)

OTHER PUBLICATIONS

U.S. Patent Application Serial No. 08/276,219, entitled "Medical Appliances For the Treatment of Blood Vessels By Means of Ionizing Radiation", filed Jun. 28, 1994, which is commonly owned by the Assignee of the above–captioned application.

(List continued on next page.)

*Primary Examiner*—John P. Lacyk
(74) *Attorney, Agent, or Firm*—Crompton, Seager & Tufte, LLC

(57) ABSTRACT

The appliance comprises radioactive radiation means formed by a coiled filament of radioactive material a proximal part of which is formed by a coiled filament having a pitch larger than that of the coiled filament. Coiled filament is for meshing with thread formed at the distal end of a guidewire.

8 Claims, 8 Drawing Sheets

U.S. PATENT DOCUMENTS

| | | | |
|---|---|---|---|
| 4,763,642 | 8/1988 | Horowitz | 128/1.2 |
| 4,763,671 | 8/1988 | Goffinet | 128/786 |
| 4,782,834 | 11/1988 | Maguire et al. | 128/344 |
| 4,784,116 | 11/1988 | Russell, Jr. et al. | 128/1.2 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,897,076 | 1/1990 | Puthawala et al. | 600/7 |
| 4,936,823 | 6/1990 | Colvin et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman et al. | 128/659 |
| 4,976,680 | 12/1990 | Hayman et al. | 600/7 |
| 4,976,690 | 12/1990 | Solar et al. | 604/96 |
| 4,994,013 | 2/1991 | Suthanthiran et al. | 600/8 |
| 5,030,194 | 7/1991 | Van't Hooft | 600/3 |
| 5,032,113 | 7/1991 | Burns | 604/96 |
| 5,059,166 | 10/1991 | Fischell et al. | 600/3 |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,103,395 | 4/1992 | Spako et al. | 364/413.26 |
| 5,106,360 | 4/1992 | Ishiwara et al. | 600/2 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 | 1/1993 | Fischell et al. | 600/3 |
| 5,183,455 | 2/1993 | Hayman et al. | 600/7 |
| 5,199,939 | 4/1993 | Dake et al. | 600/3 |
| 5,213,561 | 5/1993 | Weinstein et al. | 600/3 |
| 5,267,960 | 12/1993 | Hayman et al. | 604/106 |
| 5,282,781 | 2/1994 | Liprie | 600/3 |
| 5,302,168 | 4/1994 | Hess | 600/3 |
| 5,344,383 | 9/1994 | Liping | 600/3 |
| 5,354,257 | 10/1994 | Roubin et al. | 600/7 |
| 5,370,685 | 12/1994 | Stevens | 623/2 |
| 5,391,139 | 2/1995 | Edmundson | 600/7 |
| 5,395,300 | 3/1995 | Liprie | 600/3 |
| 5,405,309 | 4/1995 | Carden, Jr. | 600/3 |
| 5,409,015 | 4/1995 | Palermo | 128/772 |
| 5,411,466 | 5/1995 | Hess | 600/3 |
| 5,425,720 | 6/1995 | Rogalsky et al. | 604/198 |
| 5,429,582 | 7/1995 | Williams | 600/2 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,532,122 | 7/1996 | Drukier | 435/5 |
| 5,538,494 | 7/1996 | Matsuda | 600/1 |
| 5,540,659 | 7/1996 | Teirstein | 604/104 |
| 5,556,389 | 9/1996 | Liprie | 604/264 |
| 5,575,749 | 11/1996 | Liprie | 600/3 |
| 5,605,530 | 2/1997 | Fischell et al. | 600/3 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,624,372 | 4/1997 | Liprie | 600/3 |
| 5,643,171 | 7/1997 | Bradshaw et al. | 600/1 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlein et al. | 600/3 |
| 5,683,345 | 11/1997 | Waksman et al. | 600/3 |
| 5,688,220 | 11/1997 | Verin et al. | 600/1 |
| 5,707,332 | 1/1998 | Weinberger | 600/3 |
| 5,713,828 | 2/1998 | Coniglione | 600/7 |
| 5,720,717 | 2/1998 | D'Andrea | 604/21 |
| 5,722,984 | 3/1998 | Fischell et al. | 606/198 |
| 5,728,042 | 3/1998 | Schwager | 600/3 |
| 5,730,698 | 3/1998 | Fischell et al. | 600/3 |
| 5,782,740 | 7/1998 | Schneiderman | 600/1 |
| 5,782,742 | 7/1998 | Crocker et al. | 600/3 |
| 5,795,286 | 8/1998 | Fischell et al. | 600/3 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,816,259 | 10/1998 | Rose | 128/898 |
| 5,816,999 | 10/1998 | Bischoff et al. | 600/3 |
| 5,820,553 | 10/1998 | Hughes | 600/426 |
| 5,833,593 | 11/1998 | Liprie | 600/3 |
| 5,840,008 | 11/1998 | Klein et al. | 600/3 |
| 5,840,009 | 11/1998 | Fischell et al. | 600/3 |
| 5,840,064 | 11/1998 | Liprie | 604/96 |
| 5,843,163 | 12/1998 | Wall | 623/1 |
| 5,851,171 | 12/1998 | Gasson | 600/3 |
| 5,851,172 | 12/1998 | Bueche et al. | 600/7 |
| 5,855,546 | 1/1999 | Hastings et al. | 600/3 |
| 5,857,956 | 1/1999 | Liprie | 600/7 |
| 5,863,284 | 1/1999 | Klein | 600/3 |
| 5,863,285 | 1/1999 | Coletti | 600/3 |
| 5,865,720 | 2/1999 | Hastings et al. | 600/3 |
| 5,871,436 | 2/1999 | Eury | 600/3 |
| 5,871,437 | 2/1999 | Alt | 600/3 |
| 5,873,811 | 2/1999 | Wang et al. | 600/5 |
| 5,879,282 | 3/1999 | Fischell et al. | 600/3 |
| 5,882,290 | 3/1999 | Kume | 600/3 |
| 5,882,291 | 3/1999 | Bradshaw et al. | 600/3 |
| 5,891,091 | 4/1999 | Teirstein | 604/104 |
| 5,897,573 | 4/1999 | Rosenthal et al. | 606/224 |
| 5,899,882 | 5/1999 | Waksman et al. | 604/96 |
| 5,906,573 | 5/1999 | Aretz | 600/3 |
| 5,910,101 | 6/1999 | Andrews et al. | 600/3 |
| 5,910,102 | 6/1999 | Hastings | 600/3 |
| 5,913,813 | 6/1999 | Williams et al. | 600/3 |
| 5,916,143 | 6/1999 | Apple et al. | 600/3 |
| 5,919,126 | 7/1999 | Armini | 600/3 |
| 5,924,973 | 7/1999 | Weinberger | 600/3 |
| 5,924,974 | 7/1999 | Loffler | 600/3 |
| 5,938,582 | 8/1999 | Ciamacco, Jr. et al. | 600/3 |
| 5,947,889 | 9/1999 | Hehrlein | 600/3 |
| 5,947,924 | 9/1999 | Liprie | 604/96 |
| 5,947,958 | 9/1999 | Woodard et al. | 606/1.5 |
| 5,957,829 | 9/1999 | Thornton | 600/3 |
| 5,961,439 | 10/1999 | Chernomorsky et al. | 600/4 |
| 5,967,966 | 10/1999 | Kronholz et al. | 600/3 |
| 5,971,909 | 10/1999 | Bradshaw et al. | 600/3 |
| 5,976,106 | 11/1999 | Verin et al. | 604/96 |
| 5,997,462 | 12/1999 | Loffler | 600/3 |
| 5,997,463 | 12/1999 | Cutrer | 600/8 |
| 6,010,445 | 1/2000 | Armini et al. | 600/3 |
| 6,013,019 | 1/2000 | Fischell et al. | 600/3 |
| 6,013,020 | 1/2000 | Meloul et al. | 600/7 |
| 6,024,690 | 2/2000 | Lee et al. | 600/3 |
| 6,030,333 | 2/2000 | Sioshansi et al. | 600/3 |
| 6,033,357 | 3/2000 | Ciezki et al. | 600/3 |

FOREIGN PATENT DOCUMENTS

| | | |
|---|---|---|
| 195 26 680 A1 | 1/1997 | (DE) . |
| 197 54 870 A1 | 8/1998 | (DE) . |
| 197 24 233 C1 | 12/1998 | (DE) . |
| 197 58 234 | 7/1999 | (DE) . |
| 198 07 727 | 7/1999 | (DE) . |
| 198 25 563 | 12/1999 | (DE) . |
| 198 25 999 | 12/1999 | (DE) . |

| | | | | | | |
|---|---|---|---|---|---|---|
| 198 26 000 | 12/1999 | (DE) . | | WO 98/39063 | 9/1998 | (WO) . |
| 19829 447 | 1/2000 | (DE) . | | WO 98/40032 | 9/1998 | (WO) . |
| 0152124 | 8/1985 | (EP) . | | WO 98/46309 | 10/1998 | (WO) . |
| 0158630 | 10/1985 | (EP) . | | WO 98/55179 | 12/1998 | (WO) . |
| 0308360 | 3/1989 | (EP) . | | WO 98/57706 | 12/1998 | (WO) . |
| 0433011A1 | 6/1991 | (EP) . | | WO 99/01179 | 1/1999 | (WO) . |
| 0447745A2 | 9/1991 | (EP) . | | WO 99/02219 | 1/1999 | (WO) . |
| 0466681A1 | 1/1992 | (EP) . | | WO 99/04706 | 2/1999 | (WO) . |
| 0474994 | 3/1992 | (EP) . | | WO 99/04856 | 2/1999 | (WO) . |
| 0 514 913 A2 | 11/1992 | (EP) . | | WO 99/10045 | 3/1999 | (WO) . |
| 0 633 041 A1 | 1/1995 | (EP) . | | WO 99/21615 | 5/1999 | (WO) . |
| 0 686 342 A1 | 12/1995 | (EP) . | | WO 99/21616 | 5/1999 | (WO) . |
| 0 688 580 A1 | 12/1995 | (EP) . | | WO 99/22774 | 5/1999 | (WO) . |
| 0 696 906 B1 | 2/1996 | (EP) . | | WO 99/22775 | 5/1999 | (WO) . |
| 0 749 764 A1 | 12/1996 | (EP) . | | WO 99/22812 | 5/1999 | (WO) . |
| 0 754 472 A2 | 1/1997 | (EP) . | | WO 99/22815 | 5/1999 | (WO) . |
| 0 754 473 A2 | 1/1997 | (EP) . | | WO 99/24116 | 5/1999 | (WO) . |
| 0 593 136 B1 | 3/1997 | (EP) . | | WO 99/24117 | 5/1999 | (WO) . |
| 0 778 051 A1 | 6/1997 | (EP) . | | WO 99/29370 | 6/1999 | (WO) . |
| 0 801 961 A2 | 10/1997 | (EP) . | | WO 99/29371 | 6/1999 | (WO) . |
| 0 810 004 | 12/1997 | (EP) . | | WO 99/30779 | 6/1999 | (WO) . |
| 0 813 894 A2 | 12/1997 | (EP) . | | WO 99/34969 | 7/1999 | (WO) . |
| 0 629 380 B1 | 7/1998 | (EP) . | | WO 99/36121 | 7/1999 | (WO) . |
| 0 865 803 | 9/1998 | (EP) . | | WO 99/39628 | 8/1999 | (WO) . |
| 0 904 798 | 3/1999 | (EP) . | | WO 99/40962 | 8/1999 | (WO) . |
| 0 904 799 | 3/1999 | (EP) . | | WO 99/40970 | 8/1999 | (WO) . |
| 793158 | 4/1958 | (GB) . | | WO 99/40971 | 8/1999 | (WO) . |
| 10071210 | 3/1998 | (JP) . | | WO 99/40972 | 8/1999 | (WO) . |
| WO 99/29354 | 6/1979 | (WO) . | | WO 99/40973 | 8/1999 | (WO) . |
| WO 86/03124 | 6/1986 | (WO) . | | WO 99/40974 | 8/1999 | (WO) . |
| 9200776 | 1/1992 | (WO) . | | WO 99/42162 | 8/1999 | (WO) . |
| WO 93/04735 | 3/1993 | (WO) . | | WO 99/42163 | 8/1999 | (WO) . |
| WO 94/25106 | 11/1994 | (WO) . | | WO 99/42177 | 8/1999 | (WO) . |
| WO 94/26205 | 11/1994 | (WO) . | | WO 99/44686 | 9/1999 | (WO) . |
| WO 95/07732 | 3/1995 | (WO) . | | WO 99/44687 | 9/1999 | (WO) . |
| 9606654 | 3/1996 | (WO) . | | WO 99/49935 | 10/1999 | (WO) . |
| WO 96/10436 | 4/1996 | (WO) . | | WO 99/56825 | 11/1999 | (WO) . |
| WO 96/13303 | 5/1996 | (WO) . | | WO 99/56828 | 11/1999 | (WO) . |
| WO 96/14898 | 5/1996 | (WO) . | | WO 99/61107 | 12/1999 | (WO) . |
| WO 96/17654 | 6/1996 | (WO) . | | WO 99/62598 | 12/1999 | (WO) . |
| WO 96/22121 | 7/1996 | (WO) . | | WO 99/66979 | 12/1999 | (WO) . |
| WO 96/29943 | 10/1996 | (WO) . | | WO 00/03292 | 1/2000 | (WO) . |
| WO 96/40352 | 12/1996 | (WO) . | | WO 00/04838 | 2/2000 | (WO) . |
| WO 97/07740 | 3/1997 | (WO) . | | WO 00/04953 | 2/2000 | (WO) . |
| WO 97/09937 | 3/1997 | (WO) . | | WO 00/09212 | 2/2000 | (WO) . |
| WO 97/17029 | 5/1997 | (WO) . | | | | |
| WO 97/18012 | 5/1997 | (WO) . | | | | |
| WO 97/19706 | 6/1997 | (WO) . | | | | |
| WO 97/25102 | 7/1997 | (WO) . | | | | |
| WO 97/25103 | 7/1997 | (WO) . | | | | |
| WO 97/40889 | 11/1997 | (WO) . | | | | |
| WO 98/01183 | 1/1998 | (WO) . | | | | |
| WO 98/01184 | 1/1998 | (WO) . | | | | |
| WO 98/01185 | 1/1998 | (WO) . | | | | |
| WO 98/01186 | 1/1998 | (WO) . | | | | |
| WO 98/11936 | 3/1998 | (WO) . | | | | |
| WO 98/16151 | 4/1998 | (WO) . | | | | |
| WO 98/20935 | 5/1998 | (WO) . | | | | |
| WO 98/25674 | 6/1998 | (WO) . | | | | |
| WO 98/29049 | 7/1998 | (WO) . | | | | |
| WO 98/30273 | 7/1998 | (WO) . | | | | |
| WO 98/34681 | 8/1998 | (WO) . | | | | |
| WO 98/36788 | 8/1998 | (WO) . | | | | |
| WO 98/36790 | 8/1998 | (WO) . | | | | |
| WO 98/36796 | 8/1998 | (WO) . | | | | |
| WO 98/39052 | 9/1998 | (WO) . | | | | |
| WO 98/39062 | 9/1998 | (WO) . | | | | |

OTHER PUBLICATIONS

Tjho–Heslinga et al., "Results of ruthenium irradiation of uveal melanona", *Radiotherapy Oncology*, vol. 29, pp 33–38, 1993.

Lommatzsch et al., "Radiation effects on the optic nerve observed after brachytherapy of choroidal melanomas with 106Ru/106Rh plaques", *Graefe's Arch. Clin. Exp. Ophthalmology* vol. 232, pp. 482–487, 1994.

*Radiotherapy of Intraoculare and Orbital Tumors*, Springer–Verlak publishers, Berlin Heidelberg and New York, copyright 1993, pp. 23–30 and 363–367.

Fackelmann, "Harbinger of a Heart Attack", *Science News*, vol. 151, Jun. 14, 1997, pp. 374–375.

Raloff, "Nuclear Medicine Gets Friendlier—Experimental Therapies Seek to Posion Just the Disease", *Science News*, Bol. 152, Jul. 19, 1997, pp. 40–41.

Sutherland, "Managing Cancer Through Synergy", *Administrative Radiology Journal*, Nov. 1996, pp. 21–27.

MEDICAL DEVICE WITH RADIATION SOURCE

This is a division of application Ser. No. 08/489,464, filed on Jun. 12, 1995, now U.S. Pat. No. 5,688,220.

I. Field of the Invention

This invention relates to a medical appliance for the treatment of a portion of body vessel by ionizing radiation, comprising a radioactive radiation means, and manipulation means.

Endoluminal brachtherapy and more particularly percutaneous transluminal brachytherapy currently face difficulties for handling, energizing, transporting and sterilizing the equipment used for applying the therapy.

II. Discussion of the Prior Art

For example, U.S. Pat. No. 5,147,282 discloses a manual irradiation loading apparatus particularly suitable for intrabronchial and gynecological irradiation treatment. The apparatus comprises a lead or equivalent radiation shielding body with a longitudinally extending cable-receiving passage therein. A cable having radioactive seeds provided on one end thereof is received in the cable-receiving passage. During storage, the portion of the cable bearing the radioactive source is located in the cable-receiving passage within the shielding body. During use, a catheter placed in a patient is joined to the shielding body and the portion of the cable bearing the radioactive source material is advanced through the cable receiving passage in the shielding body and into the catheter. The disclosure provides for using commercially available cable having radioactive seeds provided on an end portion thereof or radioactive wire.

According to one embodiment, this document provides for a shielding body constructed to receive a radiation source other than a seeded cable. A shielding body is therefore constructed with a metallic tube running therein from end to end, extending through one end of the shielding body and extending through and beyond the other end thereof. This metallic tube is for allowing free passage of a plastic tandem closed at one end and containing Cesium tube sources maintained in the tandem by a plastic stopper insert. For loading the radiation sources into the patient, an empty metal tandem is positioned in the patient and a docking tube with quick release connectors of the spring clip type with actuating levers at both ends is attached, one end to the shielding body and the other end to the patient's metal tandem. Then, using a loading-retrival cable assembly, the plastic tandem containing the radioactive sources and the stopper insert is pushed through the shielding body via the docking tube and into the metal tandem inserted into the patient. The empty shielding body and the docking tube may then be temporarily removed and stored nearby.

When the irradiation treatment has been completed, the radioactive sources must be removed by means of the loading-retrival cable assembly. To this effect, the stopper insert is first removed from the plastic tandem and the docking tube and shielding body are again connected to the patient. To remove the radioactive sources the loading-retrival cable assembly comprises a steel able surrounded by a teflon tube, this steel cable being terminated by a solid tip extending out of the teflon tube and bearing against a soft rubber ring located between the solid tip and the end of the teflon tube; the other end of the steel cable is attached to a retracting mechanism comprising a return spring urging the end of the steel cable is attached to a retracting mechanism comprising a return spring urging the end of the steel cable and controlled by a set screw with eccentic lock-up. Within this configuration, the loading-retrival cable assembly is advanced through the shielding body and docking tube and stopped at the opening of the plastic tandem containing the radioactive sources and the cable solid top and soft rubber ring and passed inside the plastic tandem. The set screw of the retracting mechanism is triggered to retract the steel cable thereby forcing the solid tip to squeeze the soft rubber ring against the end of the teflon tube so that the soft rubber ring expands radially and firmly grips the inner wall of the plastic tandem. The loading-retrival cable assembly being thus connected to the plastic tandem containing the radioactive sources, one may pull the cable out of the docking tube and retrieve the plastic tandem and radioactive sources back to storage position inside the shielding apparatus. Reverse operation of the retracting mechanism disconnects the steel cable from the plastic tandem and the stopper insert maybe re-inserted into the plastic tandem.

In the case of usage of radioactive guidewires, there is the problem to safely secure the radioactive radiation source to the manipulating wire. The source can of course only be made of radiating material and will therefore always have only certain limited material properties. Another problem is that the source always has to be activated for itself without the manipulation wire. An activation together with the manipulation wire would also activate the wire, which would result in harmful radiation from the wire.

It is an object of this invention to improve the conditions of handling, energizing, transporting and sterilizing the materials used for endoluminal and more particularly percutaneous transluminal brachytherapy. It is a further object of the invention to improve such conditions by means of appliances that are simple to manufacture and easy to use. Still a further object of the invention is an equipment that is safe and devoid of hazardous structures, and which allows treatment in remote locations and narrow vessels.

To this effect, the invention complies with the definitions given in the claims,

SUMMARY OF THE INVENTION

Accordingly, the part of the radioactive radiation means making part of a detachable interlocking engagement between the radioactive radiation means and the manipulation means allows the manufacture of a tolerance free assembly which can be used without particularly precise or skill demanding manipulations. It also allows the realization of a place saving assembly capable of being inserted into very narrow vessels. And as it is not dependent on any mechanism it can be safely used for treatment of remote locations. The radioactive radiation means can be easily energized and handled separately from the advancing and removing means, whereby a simple and safe circulation of radioactive materials may be organized between the hospital and the energizing center or the manufacturer. In addition, as the radioactive radiation means may be handled alone, there is a substantial place saving in the energizing reactor, whereby a better and cheapest organization of the occupation of the reactor. In parallel, sterilization of the manipulation means can be achieved conventionally and without any particular shielding, while sterilization of the radioactive radiation means is systematically asured by the radioactive radiation. The invention thus solves the aforesaid problems by proposing a detachable connection between radiation source and manipulation wire which is formed by the radiation source itself. With this solution no complicated welding or other manipulation of the activated source is necessary. And as the radiation source can be activated for its own, separated from the manipulating wire, only the desired radiation is generated in purity.

Where the medical appliance comprises proximal recess means and stone means on the radioactive radiation means for cooperation with distal recess means and stone means arranged on the manipulation means, an assembly is achieved which allows selection at will of any desired longitudinal play in the assembly to combine a good pushability of the system with an appreciable capacity to handle narrow and tortuous vessels. And this interlocking engagement may be locked by mere insertion into a lumen.

The medical appliance may comprise proximal and distal wall means on the radioactive radiation means for cooperation with distal recess means arranged on the manipulation means, thereby achieving a detachable interlocking engagement which requires a very simple shaping of the radioactive radiation means and of the manipulation means. This interlocking engagement may also be locked by engagement into a lumen.

Where the appliance comprises proximal coil means on the radioactive radiation means for meshing with distal thread means on the manipulation means, a playless assembly is achieved which combines extreme flexibility and good pushability in a fully positive assembly which can be designed to reach the smallest dimensions.

In the case of the medical appliance comprising proximal recess means and stone means, resp. proximal and distal wall means, on the radioactive radiation means for cooperation with distal recess means and stone means, resp. distal recess means, on the manipulation means, the detachable interlocking engagement may be locked by insertion into a lumen which may extend longitudinally into a catheter, whereby safest and fastest positioning of the radioactive radiation means may be achieved into the body vessel. In the case of the medical appliance comprising proximal coil means for meshing with distal thread means of the manipulation means, the detachable interlocking engagement may be guided by insertion into a lumen which may also extend longitudinally into a catheter, thereby facilitating meshing of the thread means into the coil means if the latter have a great flexibility. And in both cases, the medical appliance further may comprise a shielding applicator means for supporting the radioactive radiation means in its orientation towards the manipulation means, thereby allowing an operator to lock the detachable interlocking engagement between the radioactive radiation means and the manipulation means by manipulating the manipulation means. This shielding applicator means also facilitates transport and circulation of the radioactive radiation means.

These and other objects of the invention will become readily apparent from the following detailed description with reference to the accompanying drawings which show, diagrammatically and by way of example only, embodiments of the invention.

DESCRIPTION OF THE PREFERRED EMBODIMENTS

Figure 1:
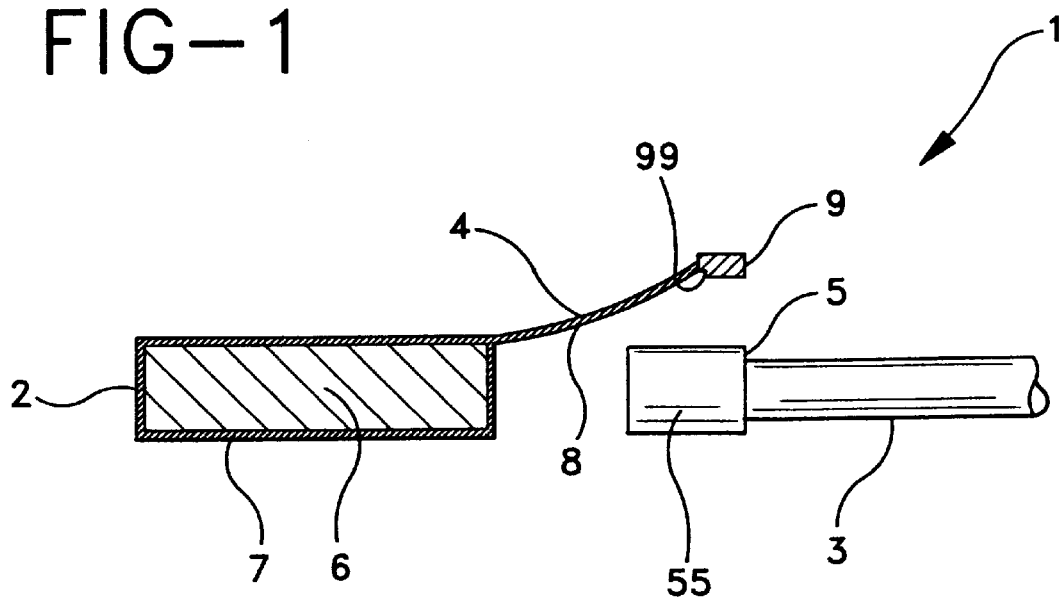
FIG. 1 is an axial cut of a first embodiment.

FIG. 1 shows a medical appliance 1 for the treatment of a portion of body vessel (not shown) by ionizing radiation, comprising a radioactive radiation means 2 and manipulation means 3 for instance for advancing, resp. removing, the radioactive radiation means 2 into, resp. from, the portion of body vessel. In this medical appliance, a part 4 of the radioactive radiation means 2 forms part of a detachable interlocking engagement between the radioactive radiation means 2 and the manipulation means 3. In the example shown, the radioactive radiation means 2 is constituted by a bar 6 of radioactive material, for instance a bar of 90 Yttrium, embedded in a cover 7 of neutral material, for instance a cover of Titanium, for non-contamination purposes.

The part 4 of the radioactive radiation means 2 is formed here by an upwardly curved elastic arm 8 terminating by a stone 9 forming a recess 99 on arm 8 which is intended to engage with a circularly shaped recess 5 formed by a stone 55 at the end of a guidewire forming the manipulation means 3. Part 9 thus forms a proximal recess and stone means elastically connected to the radioactive radiation means which is for cooperation with distal recess and stone means arranged on the manipulation means. The detachable interlocking engagement of stone 9 in recess 5 may be locked by insertion into a lumen devised into an applicator and/or catheter in which the lumen extends longitudinally, as will be described hereafter.

Figure 2:
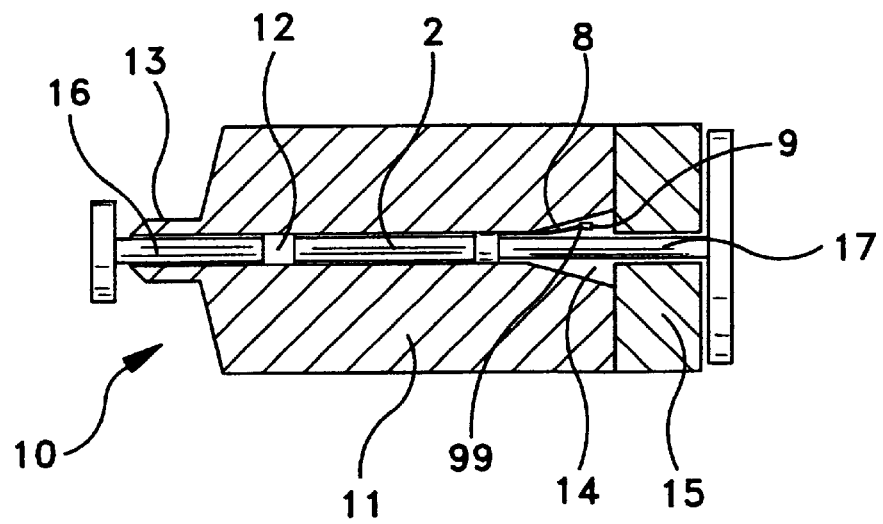
FIGS. 2 to 5 are axial cuts showing operation of the embodiment of FIG. 1.

As shown in FIG. 2, a shielding applicator 10 for supporting the radioactive radiation means 2 in its orientation towards the manipulation means 3 is formed by a base box 11 with a lumen 12 extending therethrough, ending on one side in a tapered mouth 13 and on the other side in a flared entry 14. Base box 11 is termined by a cover 15. Within the lumen 12 is positioned the radioactive radiation means 2 with its upwardly curved arm 8 extending along the flared entry 14. The tapered end 13 of box 11 is closed by a plug 16 extending into lumen 12 and the cover 15 is also closed by a plug 17 extending through flared entry 14 and into lumen 12, thereby holding the radioactive radiation means 2.

Figure 3:
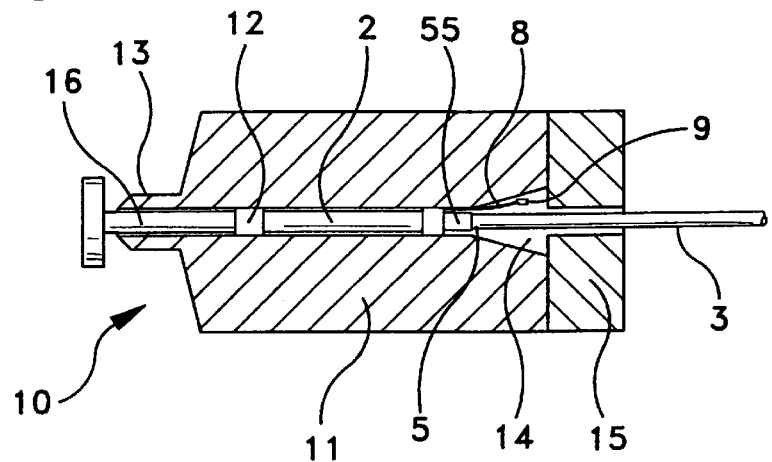
Figure 4:
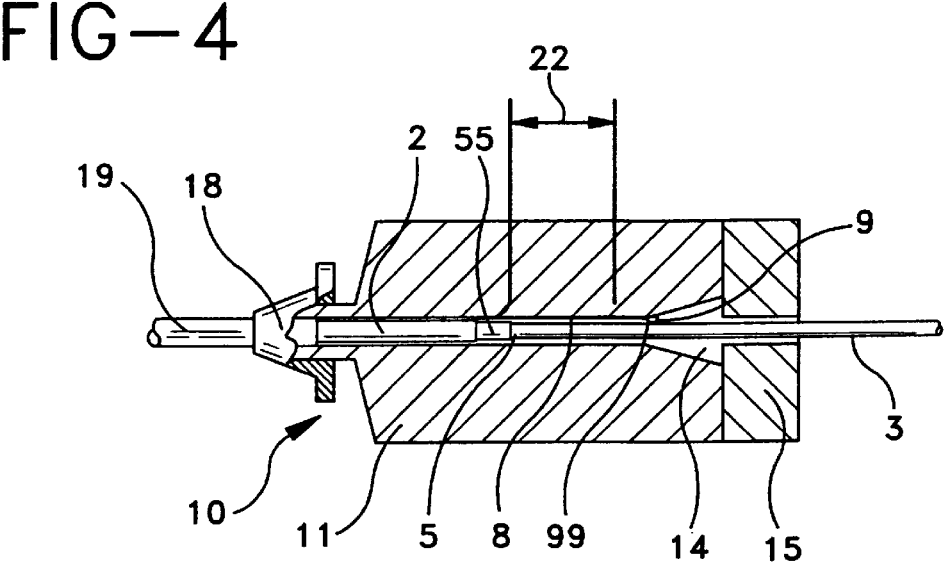
Figure 5:
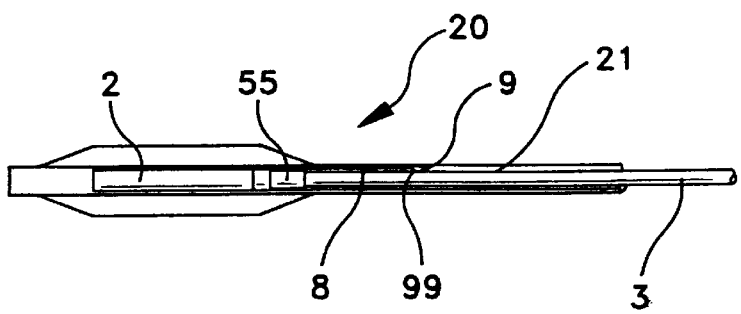

To operate the medical appliance (FIGS. 3 to 5), the plug 17 is first removed from the shielding applicator 10 and the distal end of the guidewire forming the manipulation means 3 is inserted into the flared entry 14 as shown in FIG. 3. After removal of plug 16 the tapered end 13 of box 11 is then inserted into a conventional luer connector 18 connected to the proximal end 19 of a balloon catheter 20 located in the body vessel (not shown) and having a lumen 21 extending longitudinally therethrough, as shown in FIGS. 4 and 5. By pushing the guidewire 3 towards the radioactive radiation means 2 the distal end of the guidewire abuts against the proximal end of the radioactive radiation means 2 and pushes said radioactive radiation means 2 into lumen 12, towards the luer connector 18 and into the lumen 21 of balloon catheter 20.

Passage of the radioactive radiation means 2 into lumens 12 and 21 urges arm 8 of part 4 towards the guidewire 3. At that time, reverse movement of the guidewire 3 will recover the longitudinal distance or play 22 (FIG. 4) between recess 5 and stone 9, thereby achieving the interlocking engagement of recess 99 of stone 9 and recess 5 of stone 55 which is locked by the lumens. The operator may thus lock the detachable interlocking engagement between radioactive radiation means and manipulation means by manipulating the manipulation means.

When the radioactive radiation means 2 is in the shaft of the balloon catheter 20, the shielding applicator 10 may be removed from the proximal end of the catheter and placed apart. It may also remain affixed to the luer connector 18.

After completion of the radioactive treatment, and if needed reconnection of the shielding applicator to the luer connector 18 after insertion of the proximal end of guidewire 3 through lumen 12, the guidewire 3 is withdrawn from the balloon catheter 20. Pulling of the guidewire draws proximally the radioactive radiation means 2 by interlocking of stone 9 and recess 5. When the assembly of stone 9 and recess 5 reaches the flared entry 14 of box 11, the arm 4 is freed and stone 9 withdraws from recess 5. The guidewire 3 may thus be removed from the applicator 10 while the radioactive radiation means 3 remains in the lumen 12 of applicator 10. The latter may be closed by plugs 16 and 17 and stored or sent back to the energizing reactor.

Figure 6:
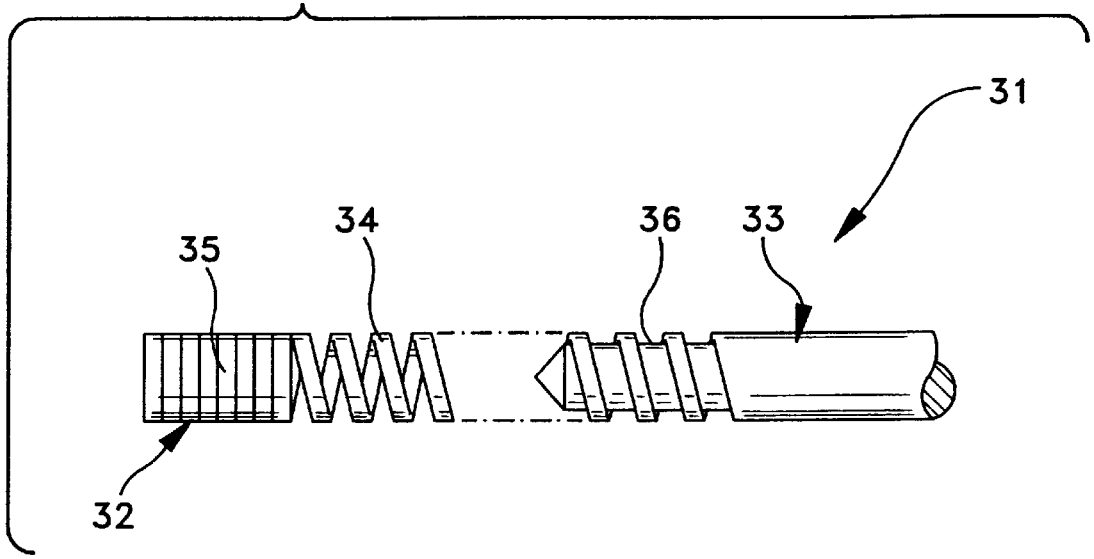
FIG. 6 is an axial view of a second embodiment.

FIG. 6 also shows a medical appliance 31 for the treatment of a portion of body vessel (not shown) by ionizing radiation, comprising a radioactive radiation means 32 and manipulation means 33 for instance for advancing, resp. removing, the radioactive radiation means 32 into, resp. from, the portion of the body vessel. In this medical appliance, a part 34 of the radioactive radiation means 32 also forms part of a detachable interlocking engagement between the radioactive radiation means 32 and the manipulation means 33.

In this example, the radioactive radiation means 32 is constituted by a coiled filament 35 of radioactive material, for instance a filament of 90 Yttrium which may be coated by a neutral material such as Titanium for non contamination purposes.

The part 34 of the radioactive radiation means 33 is formed by a coiled filament of larger pitch than the coiled filament 35 and which is intended to mesh with a thread 36 formed at the end of a guidewire forming the manipulation means 33. Part 34 thus forms a proximal coil means on the radioactive radiation means which is for meshing with distal thread means arranged on the manipulation means. The detachable interlocking engagement of coil 34 with thread 36 may me guided by insertion into a lumen devised into an applicator and/or catheter in which the lumen extends longitudinally, as well be described hereafter.

Figure 7:
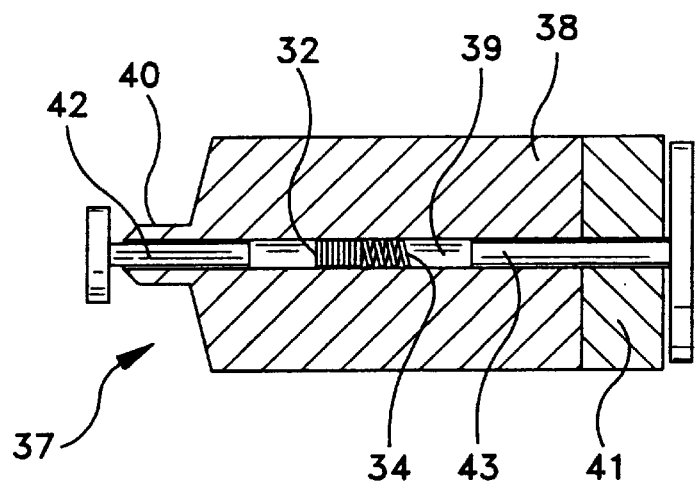
FIGS. 7 to 10 are axial cuts showing operation of the embodiment of FIG. 6.

As shown in FIG. 7, a shielding applicator 37 may also be used for supporting radioactive radiation means 32 in its orientation towards the manipulation means, being formed of a base box 38 with a lumen 39 extending therethrough, ending on one side in a tapered mouth 40 and on the other side connecting with a cover 41. Within the lumen 39 is positioned the radioactive radiation means 32 with its large pitch coil 34 properly extending coaxially in the lumen. The tapered end of box 38 is closed by a plug 42 extending into lumen 39 and the cover 41 is also closed by a plug 43 extending some distance into lumen 39, thereby holding the radioactive radiation means 32.

Figure 8:
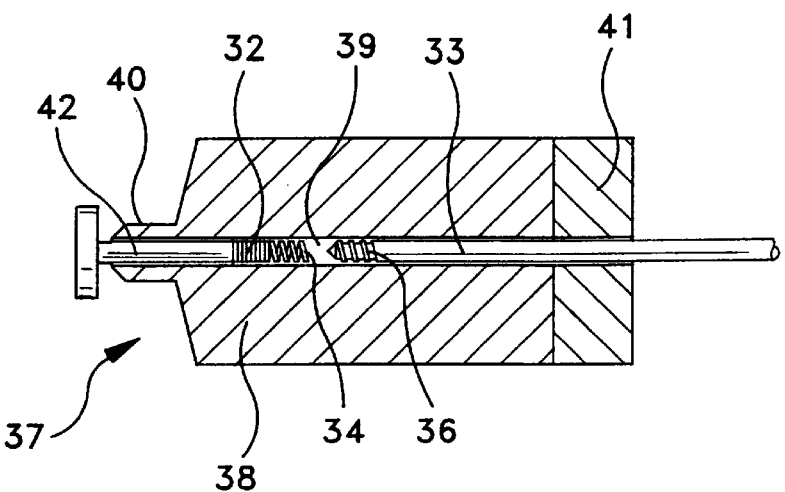
Figure 9:
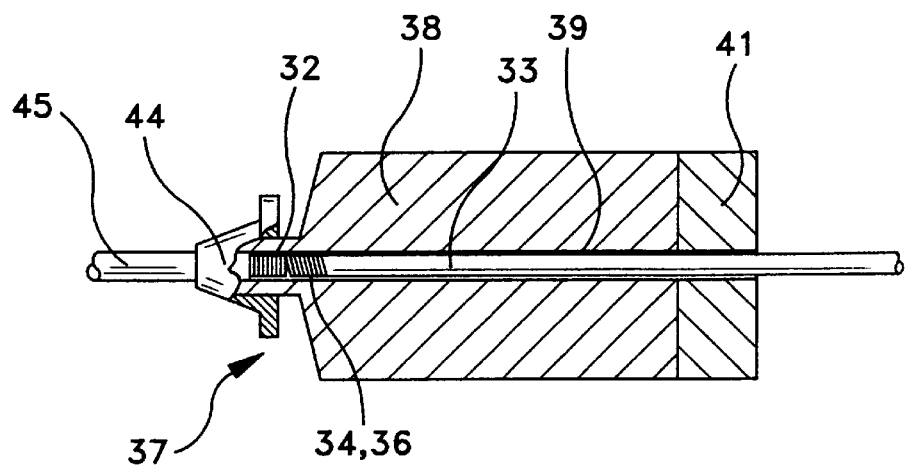
Figure 10:
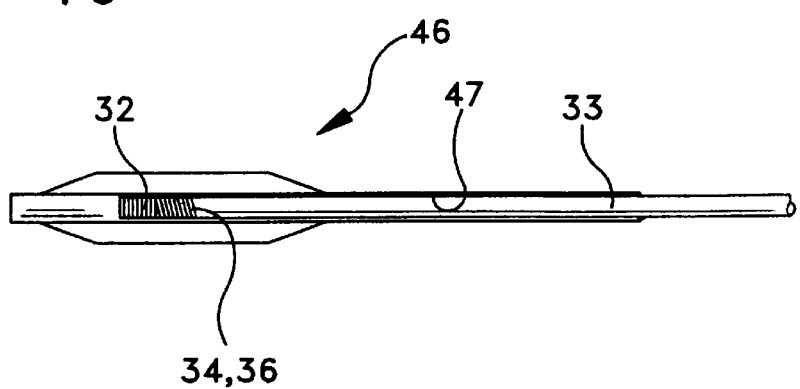

Operation of this medical appliance is as follows (FIGS. 8 to 10): plug 43 is first removed from the applicator 37 and the distal end of the guidewire forming the manipulation means 33 is inserted into the lumen 39 as shown in FIG. 8. The thread 36 of the distal end of the guidewire is then pushed against coil 34 and screwed therein. The coil 35 rests thereby against plug 42 (as shown in FIG. 8). The resulting friction is sufficient to facilitate screwing of thread 36 into coil 34. Here again the operator may thus lock the detachable interlocking engagement between radioactive radiation means and manipulation means by manipulating the manipulation means. After removal of plug 42, the tapered mouth 40 is inserted into a conventional luer connector 44 connected to the proximal end 45 of a balloon catheter 46 located in the body vessel (not shown) and having a longitudinal lumen 47 extending therethrough, as shown in FIGS. 9 and 10. By pushing the guidewire 33, the radioactive radiation means 32 may be brought at the site of treatment, as shown in FIG. 10. As for the embodiment previously described, the shielding applicator 37 may be removed or left in place once the radioactive radiation means are in the lumen 47 of the balloon catheter 46.

When the radioactive radiation treatment is completed, and if needed the shielding applicator reconnected to the luer connector 44, it suffices to withdraw the guidewire form the catheter 46 by mere pulling the guidewire 33. Once the radioactive radiation means 32 is back in the shielding applicator 37, it suffices to unscrew the thread 36 from coil 34 to remove the guidewire and thereafter close the applicator with plugs 42 and 43 while radioactive radiation means 32 remains in the applicator which may be stored or sent back to the energizing center for renewed passage into the reactor. Unscrewing of thread 36 from coil 34 may also be helped by pressure friction against plug 42 as outlined for the screwing thereof.

Figure 11:
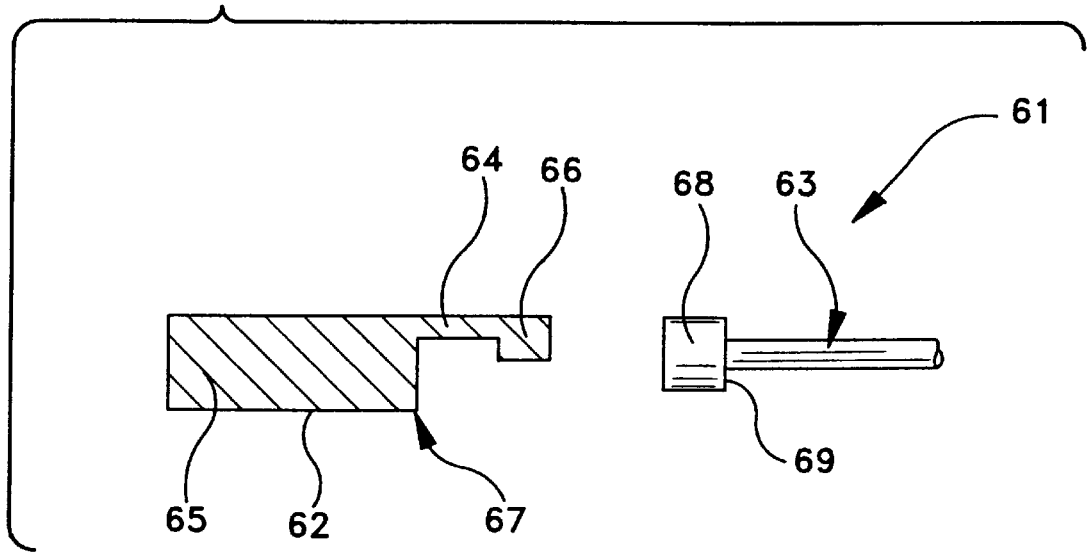
FIG. 11 is an axial cut of a third embodiment.

FIG. 11 also shows a medical appliance 61 for the treatment of a portion of body vessel (not shown) by ionizing radiation, comprising a radioactive radiation means 62 and manipulation means 63. In this embodiment as well, a part 64 of the radioactive radiation means 62 forms part of a detachable interlocking engagement between the radioactive radiation means 62 and the manipulation means 63.

In this example, the radioactive radiation means 62 is constituted by a bar 65 of radioactive material such as for instance 90 Yttrium, preferably embedded in a cover of neutral material such as Titanium (not shown).

The part 64 of the radioactive radiation means 62 is formed here by a longitudinally extending straight rigid arm terminating by a stone 66 defining a recess 67 at the end of bar 65, which is intended to engage with a recess 69 formed by a cylindrical or cubical stone 68 at the end of a guidewire forming the manipulation means 63. There is thus a proximal recess and stone means rigidly connected to the radioactive radiation means cooperating with distal recess and stone means arranged on the manipulation means. As for the embodiment shown in FIG. 1, this detachable interlocking engagement may be locked by insertion into a lumen devised in an applicator and/or catheter in which the lumen extends longitudinally, as will be described.

Figure 12:
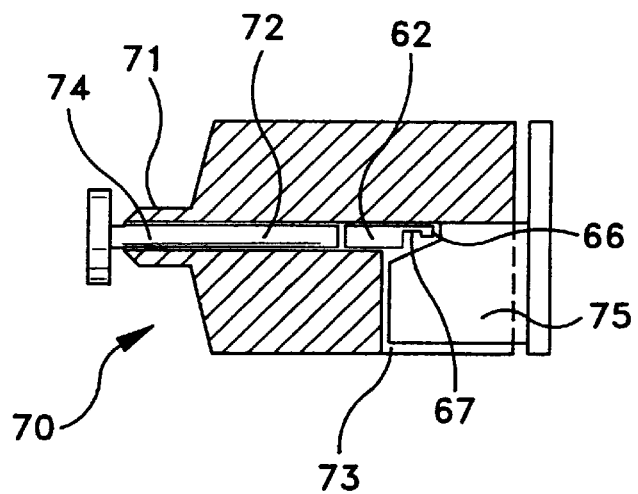
FIGS. 12 to 15 are axial cuts showing operation of the embodiment of FIG. 11.

A shielding applicator 70 (FIG. 12) for supporting the radioactive radiation means 62 in its orientation towards the manipulation means 63 is formed by a box 70 with a lumen 72 extending therethrough ending on one side in a tapered mouth 71 and on the other side in a downwardly flaring entry 73. Within lumen 72 is positioned the radioactive radiation means 62 with part 64 protruding into flaring entry 73 and recess 67 oriented downwardly. The tapered mouth 71 of box 70 is closed by a plug 74 and the downwardly flaring entry 73 is closed by a plug 75 formed to maintain the radioactive radiation means 62 in the described orientation.

Figure 13:
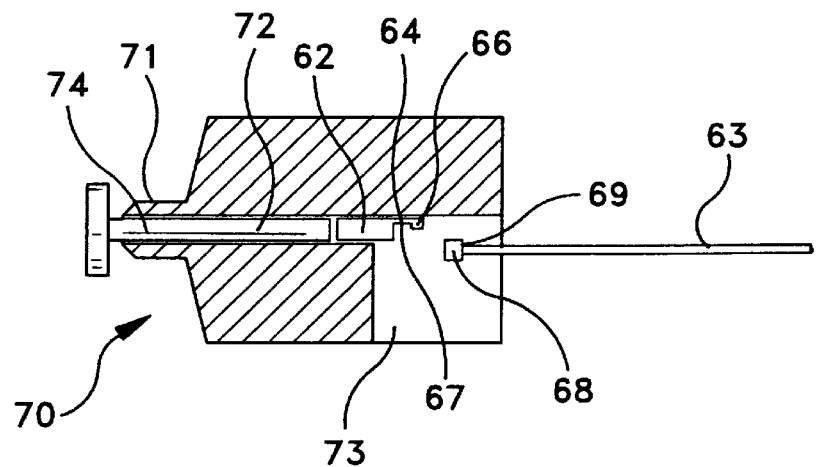
Figure 14:
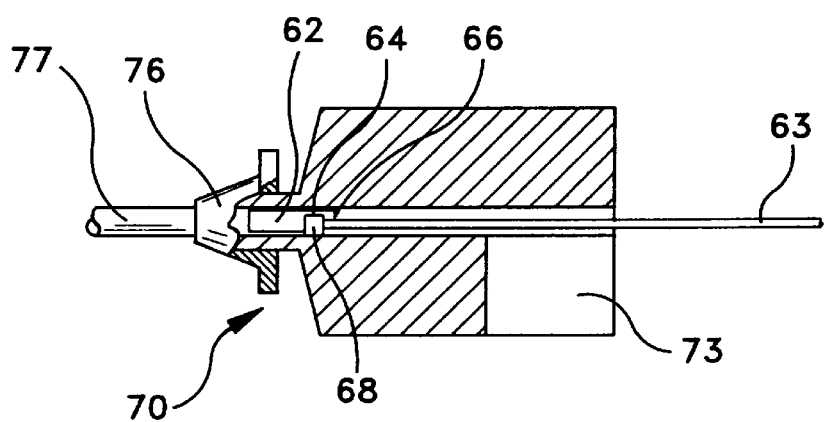
Figure 15:
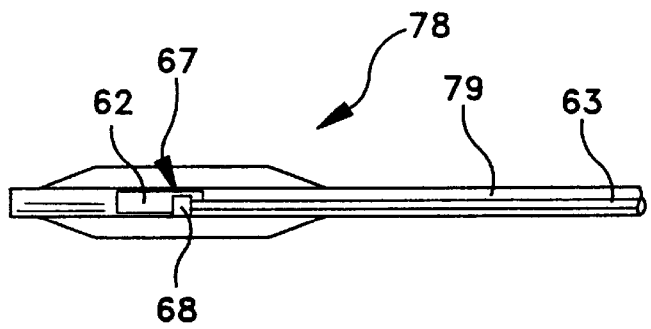

To operate this medical appliance (FIGS. 13 to 15), the plug 75 is removed and the distal end of the guidewire 63 is inserted into the flared entry 73 as shown in FIG. 13, and distal stone 68 of guidewire 63 is inserted into proximal recess 67 of part 64 of the radioactive radiation means 62. Plug 74 is removed and tapered end 71 of box 70 is inserted into a conventional luer connector 76 connected to the proximal end 77 of a balloon catheter 78 located in the body vessel (not shown) and having a lumen 79 extending longitudinally therethrough. In order to facilitate maintaining the stone 68 in recess 67, the box 70 may be turned upside-down. By pushing the guidewire 63 towards the catheter 78 the distal end of stone 68 abuts against the distal wall of recess 67 and pushes the radioactive radiation means 63 into lumen 72, towards the luer connector 76 and into lumen 79 of balloon catheter 78. Passage of the radioactive radiation means into lumens 72 and 79 locks the detachable interlocking engagement of stone 68 into recess 67. The operator thus locks the detachable interlocking engagement between radioactive radiation means and manipulation means by manipulating the manipulation means. When the radioactive radiation means 62 is in the shaft of balloon catheter the shielding applicator 70 may be removed from the proximal end of the catheter or remain affixed to the luer connector.

After completion of the radioactive treatment and if needed reconnection of the shielding applicator to the luer connector 76, the guidewire 63 is withdrawn from the balloon catheter 78. Pulling of the guidewire proximally causes recess 69 of stone 68 to engage stone 66 of part 64 thereby drawing proximally the radioactive radiation means 63 by interlocking of stone 68 and recess 67. When the assembly of stone 68 and recess 67 reaches the flared entry 73 of box 70, stone 68 is freed from recess 67, thereby allowing removal of the guidewire 63 while the radioactive radiation means means 62 remains in the lumen 72 of applicator 70. The latter may be closed by plugs 74 and 75 for storage or circulation towards the energizing reactor.

Figure 16:
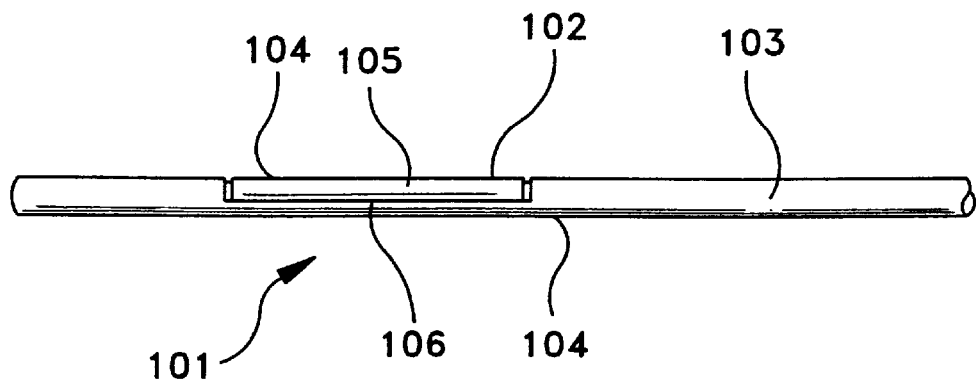
FIG. 16 is an axial view of a fourth embodiment.

FIG. 16 shows a further embodiment of the medical appliance for the treatment of a portion of a body vessel (not shown) by ionizing radiation; this appliance 101 comprises a radioactive radiation means 102 and manipulation means 103, for instance for advancing or removing the radioactive radiation means into or from the portion of body vessel. In this appliance, a part 104 of the radioactive radiation means 102 also makes part of a detachable interlocking engagement between the radioactive radiation means 102 and the manipulation means 103.

In this embodiment, the radioactive radiation means 102 is constituted by a bar 104 of radioactive material such as for instance 90 Yttrium. This bar of material may also be coated or embedded in a layer of neutral material such as a cover of Titanium.

Bar 105 is seated into a recess 106 formed at the distal end of a guidewire forming the manipulation means 103, with its proximal and distal walls 104 thereby cooperating with the distal recess 106 to assure the detachable interlocking engagement. This detachable interlocking engagement of bar 105 into recess 106 may be locked by insertion into a lumen devised into an applicator and/or catheter as will be described hereafter.

Figure 17:
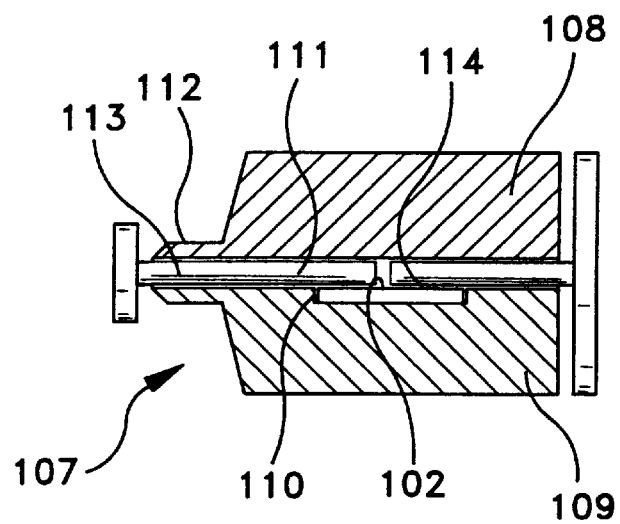
FIGS. 17 to 20 are axial cuts showing operation of the embodiment of FIG. 16.
Figure 18:
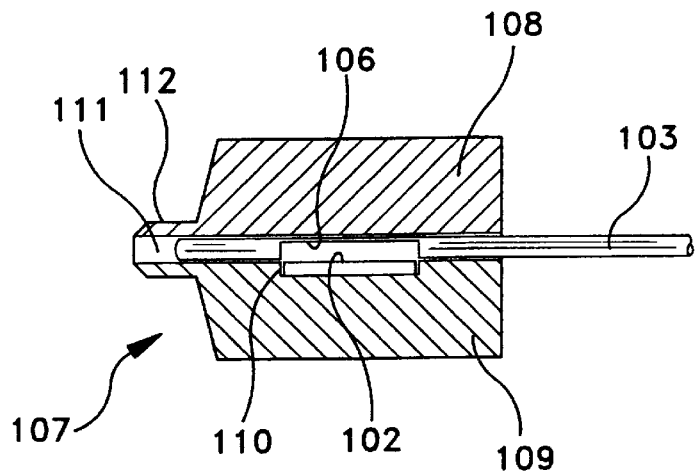

As shown in FIG. 17, a shielding applicator 107 is formed of an upper box portion 108 assembled to a lower box portion 109 with a lumen 111 extending therethrough, ending on one side in a tapered mouth 112 and on the other side ending out of the box for entry of the manipulation means 103. A recess 110 is arranged in the lower box portion 109, opening into lumen 111, which recess is sized to accomodate radioactive radiation means 102. The tapered mouth 112 of box 107 is closed by a plug 113 extending into lumen 111 and some distance over radioactive radiation means 102 and the other end of lumen 111 is also closed by a plug 114 extending therethrough and some distance over radioactive radiation means 102 thereby maintaining radioactive radiation means 102 in recess 110. Shielding applicator 107 thus supports the radioactive radiation means 102 in its orientation towards the manipulation means 103.

Figure 19:
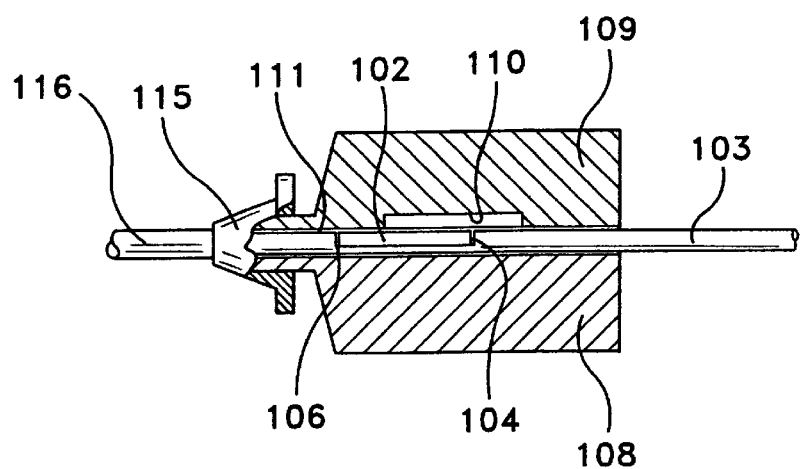
Figure 20:
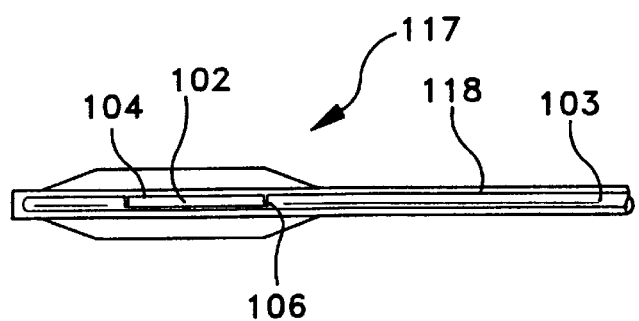

To operate the medical appliance, as shown in FIGS. 17 to 20, the plugs 113 and 114 are removed and the distal end of the guidewire 103 is inserted into the lumen 111 of box 107 and pushed therein a distance sufficient to have the recess 106 facing the radioactive radiation means 102. At that time, the box 107 and manipulation means 103 are turned upsidedown as shown in FIG. 19, whereby the radioactive radiation means 2 may fall into recess 106 of manipulation means 103. Upon further pushing manipulation means 103, the radioactive radiation means 102 further enters lumen 111. The tapered mouth 112 of shielding applicator 107 is then connected to a conventional luer connector 115 connected to the proximal end 116 of a balloon catheter 117 located in the body vessel (not shown). By pushing further the guidewire 103, the recess 106 abuts against proximal wall 104 of bar 105 and pushes the radioactive radiation means 102 through lumen 111, towards luer connector 115 and into lumen 118 of catheter 117. The operator may thus lock the detachable interlocking engagement between radioactive radiation means and manipulation means by manipulating the manipulation means. When the radioactive radiation means 102 is in the shaft of the balloon catheter 117, the shielding applicator 107 may be removed, by disassembly of box parts 108 and 109 and placed apart. It may also remain affixed to the luer connector 115.

When the radioactive treatment is completed, and if needed after reconnection of the shielding applicator to the luer connector 115, the guidewire 103 is withdrawn from balloon catheter 117; pulling of the guidewire draws proximally the radioactive radiation means 102 by interlocking of recess 106 and distal wall 104 of bar 105. The guidewire 103 may thus be pulled up to the moment radioactive radiation means 102 faces recess 110, at which time the shielding applicator 107 and guidewire 103 maybe turned upsidedown in the position shown in FIG. 18, whereby radioactive bar 105 may fall back into recess 110. The guidewire 103 may then be removed from shielding applicator 107 and plugs 113 and 114 reinserted into the ends of lumen 111, and the shielding applicator containing radioactive radiation means 102 may be stored or sent back to the energizing center.

Variants may be envisaged.

For instance, the upwardly curved elastic arm 4 may be replaced by a straight elastic arm also terminated by a stone.

The distance or play 22 (FIG. 4) between recess 5 and stone 9 may be substantially reduced to assure a more direct control of the radioactive radiation means 2.

The stone 9 and recess arrangements of FIGS. 1 to 15 may be replaced by an equivalent configuration assuring a detachable interlocking engagement, for instance an elastic hook and counter-hook interlocking with the hook arranged at the proximal end of the radioactive radiation means and the counter-hook arranged at the distal end of the manipulation means.

It is possible to replace the bar or embedded bar of radioactive material as shown in FIG. 1 by a non-solid substance, for instance powder of radioactive material such as 32 Phosphor embedded in a cover of neutral material such as Titanium. Other materials may also be envisaged such as phosphoric acid absorbed in some appropriate substance. Similarly, the bar of radioactive material may be replaced by a filament or by a coiled filament, possibly also coated by a neutral material such as Titanium.

It is also possible to replace the coiled filament 35 as shown in FIG. 6 by a straight filament, or by an embedded bar as shown in FIG. 1, or still by an embedded radioactive powder, while retaining the proximal coil means and distal thread means for the detachable interlocking arrangement as shown in FIGS. 6 to 10.

And the coil and thread interlocking engagement may also vary in its relative dimensions; for instance, the coil part 34 of FIG. 6 may have the same pitch as the coiled filament 35, the thread 36 of the manipulation means being then smaller in diameter to be threaded inside the coiled filament 35. The coil part 34 can also be on both ends of the coiled filament 35 so that the coil needs not to be oriented when filled into the shielding applicator means 37.

The bar 105 of radioactive material as shown in FIG. 16 may be replaced by two or more bars of smaller size in order to modify the intensity of the radiation and/or to modify the flexibility of the manipulation means in that region. Such bar or bars may also be replaced by coils as described hereabove.

The recess 106 formed at the distal area of the manipulation means 103 may be formed either by grinding the material forming the manipulation means or by a deformation thereof; transverse shape of this recess may be devised as desired.

The recessed configuration of the lumen 111 of shielding applicator 107 may be replaced by any other configuration allowing passage of the recessed guidewire over the radioactive radiation means to accomodate it in the recess 106; for instance a tapered lumen allowing in its large portion passage of the recessed portion 106 over the radioactive radiation means 102 and then forcing in its narrow portion the said radioactive radiation means 102 into recess 106.

What is claimed is:

1. A method for treating a body lumen comprising:
   (a) providing a non-radioactive member;
   (b) activating the non-radioactive member to make an activated radiation source;
   (c) attaching the activated radiation source about a distal portion of an elongate member; and
   (d) percutaneously disposing the distal portion of the elongate member at a treatment site.

2. The method of claim 1 further comprising the step of:
   (e) removing the radiation source from the elongate member after step (d).

3. The method of claim 1 wherein step (c) is performed while the radiation source is disposed within a shielded housing.

4. A method of claim 1 wherein the activated radiation source comprises a radioactive coil.

5. The method of claim 1 wherein the elongate member is a guidewire.

6. The method of claim 5 wherein the guidewire is adapted for insertion into a balloon catheter lumen.

7. The method of claim 1 wherein the activated radiation source includes 90 Yttrium.

8. The method of claim 4 wherein the coil is removably threaded at least partially about the distal portion of the elongate member.

* * * * *